(12) United States Patent
Larson et al.

(10) Patent No.: US 7,585,680 B2
(45) Date of Patent: Sep. 8, 2009

(54) METHOD AND DEVICE FOR MONITORING MEDICATION USAGE

(75) Inventors: Michael E. M. Larson, Minocqua, WI (US); Thomas M. Richards, Minocqua, WI (US)

(73) Assignee: Marshfield Medical Research and Education Foundation, Marshfield, WI (US)

( * ) Notice: Subject to any disclaimer, the term of this patent is extended or adjusted under 35 U.S.C. 154(b) by 844 days.

(21) Appl. No.: 10/924,105

(22) Filed: Aug. 23, 2004

(65) Prior Publication Data

US 2005/0048666 A1   Mar. 3, 2005

Related U.S. Application Data

(60) Provisional application No. 60/499,129, filed on Aug. 28, 2003.

(51) Int. Cl.
    *G01N 31/22* (2006.01)
(52) U.S. Cl. ............... 436/169; 436/111; 436/171; 436/808; 436/901
(58) Field of Classification Search .......... 436/169, 436/111; 422/58
    See application file for complete search history.

(56) References Cited

U.S. PATENT DOCUMENTS

| | | | |
|---|---|---|---|
| 4,654,310 A * | 3/1987 | Ly | 436/164 |
| 5,500,372 A | 3/1996 | Kell | |
| 5,547,878 A * | 8/1996 | Kell | 436/111 |
| 5,602,038 A | 2/1997 | Kell | |
| 5,652,146 A | 7/1997 | Kell | |
| 5,776,783 A | 7/1998 | Kell | |
| 5,908,788 A | 6/1999 | Kell | |
| 5,955,370 A | 9/1999 | Kell | |
| 6,124,136 A | 9/2000 | Kell | |
| 6,136,801 A | 10/2000 | Kell | |
| 6,492,127 B2 * | 12/2002 | Goodell et al. | 435/7.1 |
| 6,627,153 B1 * | 9/2003 | Burd et al. | 422/58 |

OTHER PUBLICATIONS

Differentiating New Marijuana Use From Residual Drug Excretion in Occasional Marijuana User, marilyn A. Huestis and Edward J. Cone. Journal of Analytical Toxicology. vol. 22, Oct. 1998.*
Differentiating New Marijuana Use From Residual Drug Excretion in Occasional Marijuana User, Marilyn A. Heustis and Edward J. Cone. Journal of Analytical Toxicology. vol. 22, Oct. 1998.*
Cone, A.J., et al., "In vivo Adulteration: Excess Fluid Ingestion Causes False-Negative Marijuana and Cocaine Urine Test Results," Journal of Analytical Toxicology, 22:460-473 (1998).

(Continued)

*Primary Examiner*—Jill Warden
*Assistant Examiner*—Dwan A Gerido
(74) *Attorney, Agent, or Firm*—Quarles & Brady, LLP

(57) ABSTRACT

The present invention provides methods for detecting and quantifying metabolites in a biological sample by measuring the concentration of a test metabolite in the sample and comparing that concentration against the concentration of the reference metabolite; enabling accurate metabolite concentration measurements to determine aberrant drug usage patterns. Also disclosed is an analytical testing device and related computer-assisted products for detecting and quantifying metabolites in a biological sample efficiently and accurately.

4 Claims, 11 Drawing Sheets

OTHER PUBLICATIONS

Fraser, A.D., et al., "Impact of Lowering the Screening and Confirmation Cutoff Values for Urine Drug Testing Based on Dilution Indicators," Therapeutic Drug Monitoring 25:723-727 (2003).

Huestis, M.A., et al., "Differentiating New Marijuana Use From Residual Drug Excretion in Occasional Marijuana Users," Journal of Analytical Toxicology, 22:445-454 (1998).

Miller, R.C. et al., "Comparison of Specific Gravity and Creatinine for Normalizing Urinary Reproductive Hormone Concentrations," Clinical Chemistry 50:924-932 (2004).

Needleman, S.B., et al., "Creatinine Analysis in Single Collection Urine Specimens," Journal of Forensic Sciences 37:1125-1133 (1992).

Preston, K.L., et al., "Methadone and Metabolite Urine Concentrations in Patients Maintained on Methadone," Journal of Analytical Toxicology, 27:332-341 (2003).

Wilkins, J. N., "Quantitative Urine Levels of Cocaine and Other Substances of Abuse," pp. 235-252.

* cited by examiner

METHOD AND DEVICE FOR MONITORING MEDICATION USAGE

CROSS-REFERENCE TO RELATED APPLICATIONS

This application claims the benefit of U.S. Provisional Patent Application Ser. No. 60/499,129, filed on Aug. 28, 2003.

STATEMENT REGARDING FEDERALLY SPONSORED RESEARCH OR DEVELOPMENT

Not applicable.

BACKGROUND OF THE INVENTION

It is important for clinicians to be informed of a patient's inappropriate use of prescribed/nonprescribed medications and/or illicit drugs to be able to properly manage their patient's care. As such, strict adherence to pharmacological dosage regimens is a prerequisite to the success of most treatments, particularly in patients in drug abuse programs or chronic pain programs. Although drug screening specimen collection procedures have been used to ensure specimen integrity, patients demonstrate considerable ingenuity in their efforts to defeat the testing process (1-4). Methods used by patients for avoiding drug misuse detection have included: diversion, excessive water consumption, ingestion of diuretics (e.g., herbal teas) and urine substitution. Individuals who divert pain medication will often "hold" a few pills to be taken before a physician visit (the "white lab coat" effect). This allows the medication to show up in their system in order to ensure that the physician renews the prescription, thereby allowing them to continue diverting the medication.

Individuals will also overuse medications, often gaining it from multiple sources. These individuals often pass the basic screening tests performed at a clinic and continue to receive the medication. Furthermore, patients treated with narcotics for the management of chronic pain also have been documented to under report their use of medications, especially for the opioid class of medications (5-11). Thus, to properly manage patient care, clinicians use external sources of information such as interviews with spouses, review of medical records, input from prescription monitoring programs, and testing of biological samples (e.g., urine) to detect inappropriate use of prescribed and nonprescribed medications, as well as, illicit drugs.

It has been previously reported that urine testing has the greatest potential for determining true compliance (12). The major problem facing urine testing is the large amount of variance in urine drug concentrations, mostly due to variations in hydration and urinary output volume (44, 45, 34). In a well-hydrated person, the level of drug metabolites per milliliter may be quite small, while a poorly hydrated person will show significantly higher levels of metabolites per milliliter. Studies have reported that if hydration is controlled, the drug metabolite level will be more consistent and accurate for urine testing. It has also been suggested that creatinine normalization may be used in correcting for variations in metabolite urine tests (13, 17, 35, 36, 34, 40, 42, 44, 46); however, others have been skeptical of this practice (41, 45).

Creatinine is a metabolite of creatine, and is an end-product of muscle metabolism excreted in the urine. Creatinine formation and excretion are directly proportional to total muscle mass and are roughly proportional to body weight. Creatinine is excreted in relatively constant amounts of 1.0 to 2.5 g/day regardless of urinary volume (14, 15). Also normalization of the excretion of a drug to the creatinine concentration reduces the variability of analyte measurement attributed to urine dilution.

Use of creatinine to reduce variance due to dilution has been suggested in the literature. However, most of these reports focus on illicit drug abuse where the concept of dose-specific use of the urine screening does not apply due to non-uniform doses and delivery systems of the illicit drugs being studied, i.e., cocaine and marijuana (16) or have not attempted to develop a normative database with confidence intervals or regression models (42). Literature in this field has also pointed to the use of urine creatinine as one method for possible adjustment that could be made in, for example, a one-step dilution protocol, but which may produce spurious results when urine creatinine is either extremely high or low (17).

Few, however, have attempted to employ use creatinine to adjust for hydration in order to monitor how a prescription drug is being used. Manno et al., reported that the Syva EMIT®-d.a.u. urine cannabinoid assay (Dade Behring, Palo Alto, Calif.) could be successfully used for detecting marijuana use patterns in a urine surveillance program if creatinine was used to reduce variance due to hydration (26). It was also reported that a delta-9-tetrahydrocannabinol-9-carboxylic acid (THCA)/creatinine ratio should decrease over time when there is no new use and a recommendation was made that when comparing results, the THCA/creatinine ratio should decrease by 50% every 2-10 days depending on the individual. More recently studies have confirmed the usefulness of the THCA/creatinine ratio under controlled-dosing conditions with marijuana smokers (37, 38). For example, it is believed that sequential creatinine normalized urine drug concentrations could predict whether marijuana exposure had re-occurred or if the presence of THCA in urine was due to continued clearance from the body in 85% of the cases. Reports have also shown that ratios in a light or infrequent user can decrease faster than in a heavy or frequent user. Some research has shown the value of using creatinine when looking at urine testing for cotinine and the effects of passive smoke inhalation (43); however, others have remained skeptical about this benefit (41).

Still other studies have attempted to develop a urine drug screen protocol by performing dose specific analyses that identified possible improper users, but have downplayed the importance of those findings (42). In these studies, the addition of a ratio of EDDP metabolite to methadone dose and then dividing that by the urine creatinine (i.e., [EDDP/methadone dose]/urine creatinine) may have disrupted the analysis and lessened the overall value of the correction. Urine creatinine has been recommended for use in the fields of illicit drug use (e.g., cocaine, marijuana, etc.). However, it has never been used to develop dose-specific confidence intervals or regression analyses that would allow clinicians to verify patient medication use that is consistent with proper use of the prescription through urine testing, with the exception of the above noted study that had the described flaws. To date no researchers have attempted to develop a urine drug screen protocol for abusable prescription medications that would enable dose specific testing and allow identification of proper vs. improper use of the medication in question. Rather, to date, a test result is purely negative or positive as to the presence or absence of a drug metabolite in the urine. Accordingly, it would be useful to develop a method to assess with confidence patient adherence to prescribed drug treatment regimens.

BRIEF SUMMARY OF THE INVENTION

The present invention is summarized as a method for detecting and quantifying at least one metabolite in a biological sample having a test metabolite. The method is carried out by contacting the biological sample with a device capable of distinguishing between the test metabolite and a reference metabolite; detecting the presence of at least one test metabolite in a biological sample; and quantifying the concentration of at least one test metabolite in a biological sample by comparing a ratio between a set of unknown data from the test metabolite versus a set of known normative data specific to the reference metabolite. The method of the present invention enables improved clinical accuracy of protocols used in testing biological samples, such as, urine testing.

One aspect of the present invention is to use the ratio between the test metabolite and reference metabolite to identify non-adherence to a prescribed medication regimen.

Another aspect of the present invention is to develop dose related normal distribution curves or confidence intervals, allowing a physician to quickly determine whether prescribed medication has been used in a manner consistent with the prescription.

Another aspect of the present invention provides an analytical device for detecting and quantifying the concentration at least one metabolite in a biological sample.

Another aspect of the present invention provides a test strip for detecting and quantifying metabolites in a biological sample.

Another aspect of the present invention provides for computer-related products, suitably in the form of software and hardware for accurately monitoring prescription adherence by reducing the variability of metabolite concentrations due to dilution for improved clinical accuracy of urine testing protocols.

In this aspect, the invention provides for computer programs, internet and intranet products used to compare and statistically analyze, for example, a new urine screen result with the normative data set to obtain improved clinical accuracy.

Also in this aspect, the invention provides, that these computer-assisted products are capable of interacting and updating the normative database and statistical features of that database through a "self-correction" mechanism, such that when each new observation is added into the database, the confidence intervals and regression equations are automatically corrected with respect to the urine reference sample in the normative dataset and the specific attributes of the urine screening elements.

In yet another aspect, the invention provides a kit for monitoring nonadherence to a prescribed medication regimen, wherein at least one or several drugs may be detected simultaneously.

Other objects, features, and advantages of the invention will be readily apparent from the following detailed description taken in conjunction with the figures.

Figure 1:
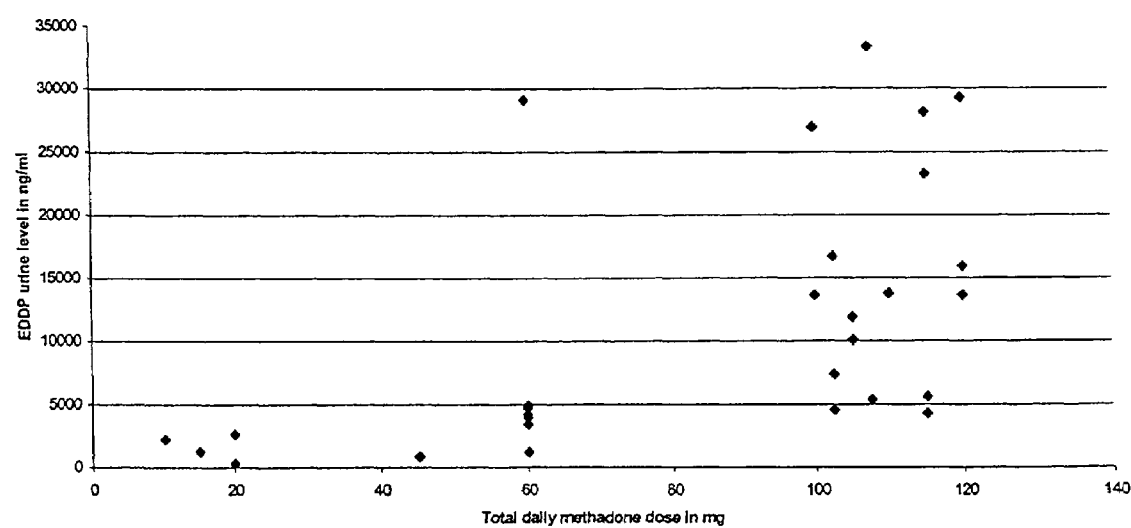
FIG. 1 is a graph showing uncorrected urine EDDP levels for confirmed daily methadone doses.

Other advantages and a fuller appreciation of specific adaptations, modifications, and physical attributes will be gained upon an examination of the following detailed description of the various embodiments, taken in conjunction with the appended claims.

DETAILED DESCRIPTION OF THE INVENTION

The present invention is based on the observation that currently available protocols for testing biological samples, such as for example, urine are insufficient for determining accurate concentrations of common metabolites corresponding to prescribed drugs. The major difficulty in urine testing is the variability in concentrations of a metabolite of interest, depending on the level of hydration of an individual at the time of testing. Accordingly, the present invention provides a novel method for accurate and efficient detection and quantification of at least one metabolite, which is specific for a prescribed medication. This method is capable of taking into account hydration-based dilution changes by developing normal distribution curves or confidence intervals. Thus, the present invention can substantially improve the ability of a clinician to monitor and confirm whether a patient has been using the medication in a manner which is consistent with the prescription.

As such, the following is a more detailed description of the various embodiments of the invention including definitions and examples.

In the present context the term "biological sample" refers to urine, blood, saliva, sweat, and spinal and brain fluids, or a combination thereof.

Also as used herein, the term "test metabolite" is intended to indicate a substance the concentration of which in a biological sample is to be measured; the test metabolite is a substance that is a by-product of or corresponds to a specific prescribed drug. The term "reference metabolite" is intended to indicate a substance used to calibrate or normalize the test metabolite against which the test metabolite is measured to determine test metabolite concentration levels; it is also a substance that corresponds to a specific prescribed drug.

The term "prescribed drug" refers to a variety of common drugs, including but not limited to common opioids, common stimulants, and common benzodiazepines. It is generally known that the drugs may have multiple combinations of common urinary metabolites and different methods for measuring the metabolites. Table 1 provides a non-limiting list of common drugs and the corresponding readily quantifiable metabolites in biological samples, such as urine.

TABLE I

| COMMON DRUGS | COMMON METABOLITES |
|---|---|
| COMMON OPIOIDS | |
| OxyContin ® | oxycodone |
| MS Contin | morphine |
| Kadian | morphine |
| Avinza | morphine |
| codeine | codeine and morphine |
| methadone | EDDP |
| Duragesic Patch | fentanyl |
| Darvocet N-100 | propoxyphene |
| hydrocodone | hydrocodone |
| COMMON STIMULANTS | |
| Ritalin/methypehnidate | amphetamine |
| Dexedrine/dextroamphetamine | amphetamine |
| COMMON BENZODIAZEPINES | |
| Valium/diazepam | diazepam/temazepam |
| Restoril/temazepam | temazepam/diazepam |
| Xanax/alprazolam | alphahydroxyalprazolam |
| Ativan/lorazepam | lorazepam |

The term "drug metabolite/creatinine ratio" refers to the ratio that is comprised of the amount of a specific metabolite of a specific drug found in a urine sample as measured by a specific test, usually stated in ng/ml divided by the amount of urine creatinine found in the urine sample as measured by the assay of urine creatinine, usually stated in dL/ml.

Applicants envision that although urine creatinine has been identified as one method of adjusting for hydration, and the method of choice at this time, other methods and metabolites may become available to allow improvement in the adjustment for hydration, which could lead to improvement in the overall predictive ability. The present application encompasses those methods and metabolites that may become available to enable improvement in the adjustment for hydration.

The term "regression equation" refers to a technical statistical procedure by which two or more variables are shown to be consistently related that allows one or more variables to predict the corresponding value of the other variable and is one procedure that allows these predictions to occur.

The term "test strips" or "analytical test strips" refers to an in vitro diagnostic tool designed to detect the presence of drugs of abuse with particular sensitivity and clarity. It is intended for use in research and educational institutions, hospitals, clinical laboratories, substance abuse clinics, law enforcement agencies, and for individuals or companies doing drug screening programs.

The term "normative database" refers to the concept of a collected set of data that is related to the specific population it is intended to predict. Statistical analysis of such a set of data, enables a person of ordinary skill in the art to perform predictive analysis based on the norms of the data set under the basic assumptions set forth by statistical analysis.

The term "self-correction" refers to the concept where each new observation (or piece of data) is subsequently added into the normative database discussed herein above as it occurs, which leads to improvement of the norms from that database. This leads to a normative database and statistical analyses that more consistently describe the true population it is intended to describe and ultimately predict.

Figure 5:
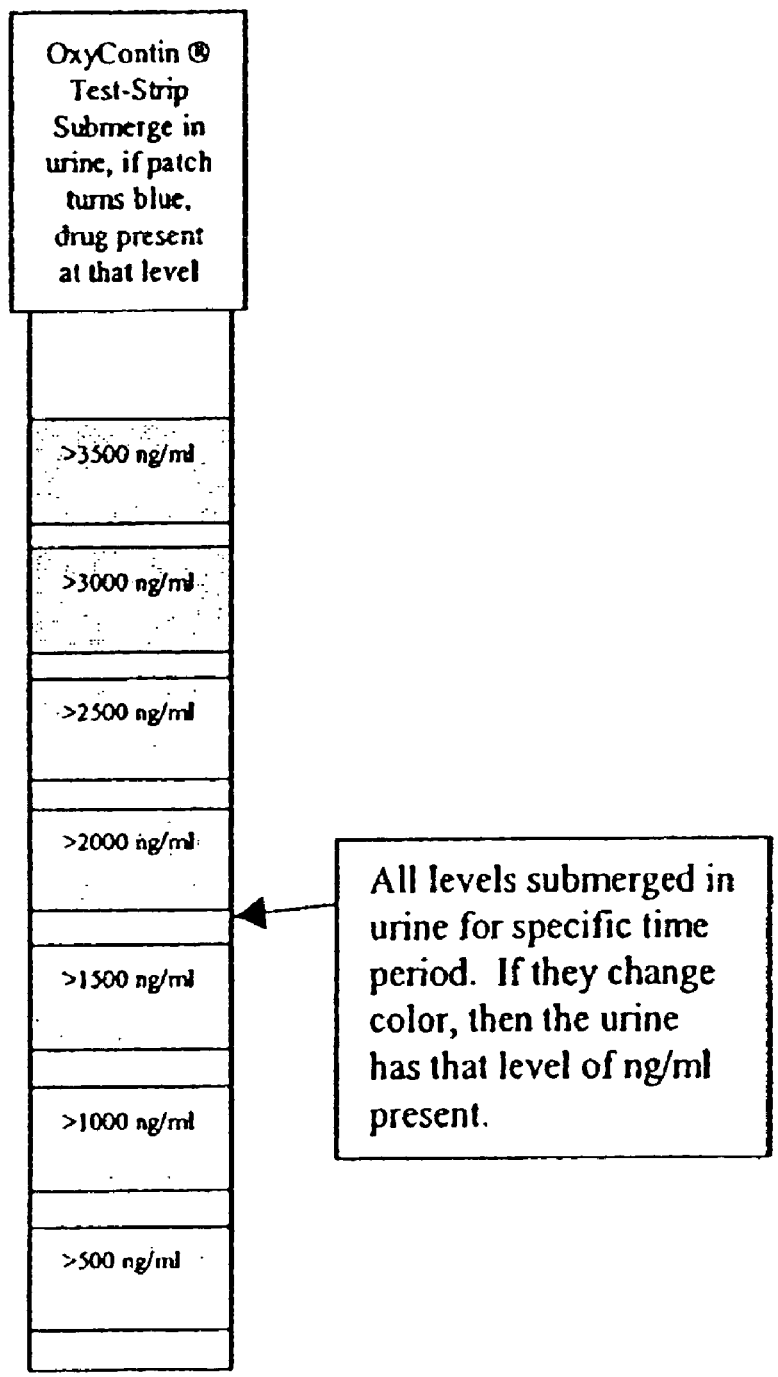
FIG. 5 depicts a flexible multi-level, vertical, one-sided test strip for determining metabolite concentration in urine.
Figure 8:
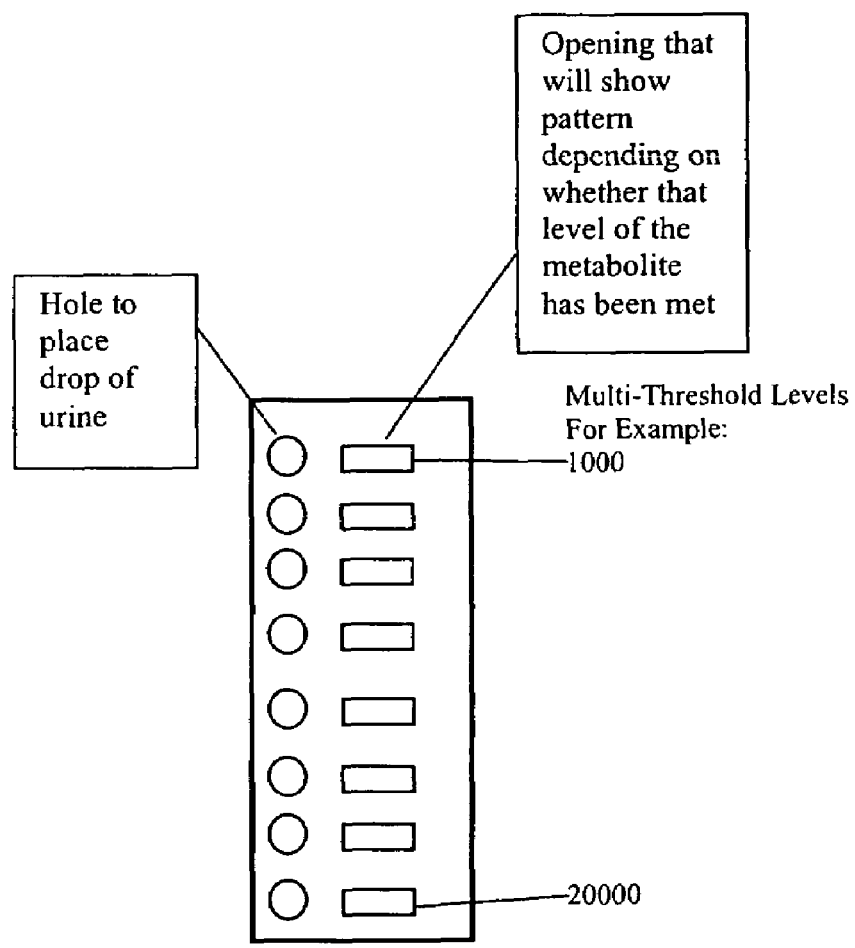
FIG. 8 depicts a hard multi-level test strip for determining urinary metabolite concentration.

Generally, in practicing the present invention, there are several different embodiments that can be used to determine the presence and concentration of at least one or more metabolites in a biological sample. For example, a metabolite concentration can be derived by use of a test strip which is capable of being flexible so as to be submerged readily into a biological sample. The test strips may be either one-sided or multi-sided and vertical in nature, as in FIG. 5 or horizontal in nature, as in FIG. 6. It is envisioned that the test strip may also be housed in a hard plastic case with an opening for introduction of a biological sample such as a "drop" of urine and a rectangular opening for display of the results (e.g., see SunLine® in vitro urine drug screening test strips, described in U.S. Pat. Nos. 5,238,652; 6,046,058; 5,962,336; and 6,372,516). However, in contrast to the SunLine® test, the test strips of the present invention have a multi-threshold and multi-level arrangement as is shown in FIG. 8.

It is also envisioned that the test strips of the invention may be prepared in the conventional manner as described in U.S. Pat. Nos. 6,210,971 and 5,733,787 to Bayer Corporation (Elkhart, Ind.) (incorporated herein in its entirety). For purposes of this invention, a test strip may be characterized as an absorbent substrate capable of immobilizing metabolites bound to a layer of support material. Well-known solid phase supports may include paper, cellulose, fabrics made of synthetic resin, e.g. nylon or unwoven fabric. The absorbent material is typically bound to a layer of support material such as glass fiber or a synthetic polymer sheet to provide structural support. Those skilled in the art of analytical test devices are aware of many other suitable solid phase supports for binding metabolites or are able to ascertain the same by use of routine experimentation.

In another embodiment the present invention may be useful for clinicians who practice in rural areas. For example, a slide-rule may be developed from normative data for measuring the concentration level of a type of prescribed drug.

In yet another embodiment, the invention provides analytical test devices, such as test strips in portable kits for determining metabolite concentrations at multiple levels using non-invasive and visually detectable methods. In this embodiment, the kit may include an analytical device for measuring the metabolite concentrations at multiple levels, as well as instructions for use of the kit components.

Other embodiments of the above and present invention are further illustrated by the following examples.

EXAMPLES

Example 1

Monitoring of Methadone Treatment

This example describes how a drug metabolite/urine creatinine ratio in patients on chronic methadone therapy (either for pain or for opioid addiction) could be used to improve the ability of clinicians to predict appropriate use of prescribed medication, as well as detect and quantify inappropriate use. Accordingly, a regression model with narrow confidence intervals and high coefficients of determination over a clinically significant range of prescribed dosages was established. This regression model was used to compare predicted urine metabolite levels for a prescribed regimen against actual metabolite levels revealing nonadherence to a given regimen to improve monitoring of medication usage.

Subjects

The charts of patients receiving methadone treatment for either substance abuse or chronic pain over a three month time period were reviewed. For inclusion in the study, the records were required to contain age, height and weight data, a specified methadone dosing regimen, and urine samples that included quantitative urine creatinine and EDDP: 2-ethylidene-1,5-dimethyl-3,3-diphenylpyrrolidone (methadone metabolite) levels. Prior to chart abstraction of qualifying patients, individual patient consent was obtained according to Institutional Review Board protocols. Any patient not agreeing to allow their records to be reviewed for this project was excluded from analysis. For consenting patients, in addition to the information listed above, any clinical notes relevant to patient drug regimen adherence or conditions expected to effect methadone metabolism were recorded.

Urine Collection

Weekly random urine screens to reveal common drugs of abuse were required of all methadone maintenance patients. All chronic pain patients signed an opioid agreement that required random urine screens for: 1) the level of the drug they were prescribed; 2) any other opioid medications; and 3) any street or illicit drug.

Urine was collected following a standard protocol for random urine screening. Clinic drug abuse or chronic pain patients were provided 30 mL specimen cups with temperature-sensitive strips. If urine temperature was identified to be appropriate for a "fresh" urine specimen, it was transferred to the laboratory for determination of a specific urine creatinine level and a general "Drug of Abuse" (also referred to as a prescribed drug) test that included EDDP quantitation via GC-MS analysis.

Creatinine Determinations

Creatinine levels were determined employing the Jaffe reaction (DRI® Creatinine-Detect; Microgenics Corp., Fremont, Calif.), whereby a red creatinine-picrate complex is formed (40). The rate of formation of the color product is measured using bichromatic pairing (absorbance at 505 nm minus nonspecific absorbance at 570 nm). Samples were colorimetrically analyzed on a Hitachi 717 analyzer (Hitachi Chemical Diagnostics, Inc., Mountain View, Calif.). The reaction rate was used to construct a linear standard curve from which the concentration of creatinine is calculated.

EDDP Determinations

Aliquots of the urine specimens are first screened for drugs of abuse by a routine immunoassay, such as ELISA, known in the art. Each presumptive positive specimen was tested as a confirmation. In the case of methadone, EDDP was quantitatively measured by gas chromatography/mass spectrometry (GC-MS) with selected ion monitoring (SIM) (18-21). For calibration, EDDP was spiked into certified negative urine at a concentration of 300 ng/ml. For test samples, an internal standard (D3-EDDP) was added, the urine was alkalinized by addition of strong base, and EDDP was extracted with organic solvent. Because EDDP has no polar functional groups, derivatization was not required. The organic extract was dried under $N_2$, reconstituted, and analyzed. The fragment ions that were monitored are as follows:

TABLE II

| Metabolite | Quantitating Ion | Qualifying Ion |
|---|---|---|
| EDDP: | 277 | 276 |
| | | 262 |
| D3-EDDP: | 280 | 265 |

The internal standard makes a small contribution to the analyte ion chromatograms, especially to the 262 ion. This limits the sensitivity of the assay to a 10 ng/ml level of detection.

Use of Urine Creatinine to Adjust for Hydration

EDDP/creatinine ratios were calculated by dividing the EDDP level (ng/ml) by the urine creatinine level (mg/dL).

Statistics

Regression analyses were used to model EDDP and the EDDP/creatinine ratio from valid urine screening results as functions of methadone dose, body size, gender, and age. All analyses were conducted in a repeated measures [mixed linear model (24)] framework to allow for correlation among multiple observations from the same patient. Backward selection was used to remove non-significant terms from the model when considering additional factors, and the coefficient of determination ($R^2$) was reported as a measure of model fit. Plots of the data and analyses of the residuals and predicted values from the regression models were used to ensure that the final models adequately represented the observed data, and 95% prediction limits (see, J. Neter and W. Wasserman; Applied Linear Statistical Models, Homewood, Ill.: Richard D. Irwin (1974), which discusses confidence limits for a single new observation) were calculated. Results in this report were deemed statistically significant at the 5% level ($p<0.05$). Body surface areas (BSA) were calculated according to the Mosteller formula (23, 24):

$$BSA(m^2) = ([height(cm) \times weight(kg)]/3600)^{1/2}$$

Lean body weights (LBW) were calculated as follows (24):

$$LBW(men) = (1.10 \times weight(kg)) - 128 \times (weight^2/(100 \times height(m))^2)$$

$$LBW(women) = (1.07 \times weight(kg)) - 148 \times (weight^2/(100 \times height(m))^2)$$

Patient Characteristics

Eight patients were identified that met the aforementioned inclusion criteria. One of those chose not to participate. The remaining subjects were either patients on methadone maintenance for opioid addiction (3 subjects, all females) or chronic pain patients who were on methadone for pain control (4 subjects, 3 males and 1 female). The specific characteristics of each of the patients used in this study is provided in TABLE III shown herein below

TABLE III

| Subject | Age | Type of Treatment Program | Dose Range per day | Urine Screen Collections | Manner of Collections | Daily Dose Confirmation | Other Patient Characteristics |
|---|---|---|---|---|---|---|---|
| 1 | 27/28 year old female | Methadone Maintenance | 102.5 to 120 mg | 10 | 8 occurring on a day after an observed dose and 2 occurring at the end of her miscarriage likely resulting in substantial changes in metabolism, producing an aberrant result | Yes | Experienced a pregnancy that ended in miscarriage while on 120 mg daily |

TABLE III-continued

| Subject | Age | Type of Treatment Program | Dose Range per day | Urine Screen Collections | Manner of Collections | Daily Dose Confirmation | Other Patient Characteristics |
|---|---|---|---|---|---|---|---|
| 2 | 25 year old female | Methadone Maintenance | 102.5 to 120 mg | 9 | 8 occurring following an observed dose and 1 occurring following reported hoarding of medication on the day prior to specimen collection producing an aberrant result | Yes | |
| 3 | 29 year old female | Methadone Maintenance | 60 mg | 9 | 5 occurring on a day after an observed dose, 4 occurring on a day after she did not take methadone the previous day | Yes | |
| 4 | 34 year old female | Chronic pain patient | 15 to 60 mg | 3 | A total of 3 urine screens met criteria, 1 occurred after 5 mg every 8 hours (15 mg total daily; 1 occurred after 10 mg every 12 hours (20 mg total daily); and 1 occurred after 30 mg every 12 hours (60 mg total daily) | No (patient reported taking the medication as prescribed) | |
| 5 | 41 year old female | Chronic pain patient | 10 to 45 mg | 2 | 1 occurred after 5 mg every 12 hours (10 mg total daily) and 1 occurred after 15 mg every 8 hours (45 mg total daily) | No (patient reported taking the medication as prescribed) | |
| 6 | 51 year old male | Chronic pain patient | 15 mg every 6 hrs (60 mg total daily) | 1 | | No (patient reported taking the medication as prescribed) | |
| 7 | 49 year old male | Chronic pain patient | 15 mg every morning and 5 mg every evening (20 mg total daily) | 1 | | No (patient reported taking the medication as prescribed) | |

Data Subset

For establishment of a regression model for the prediction of methadone intake from selected clinical parameters, data known to be aberrant were excluded from initial analysis.

Regression Analysis

Figure 2:
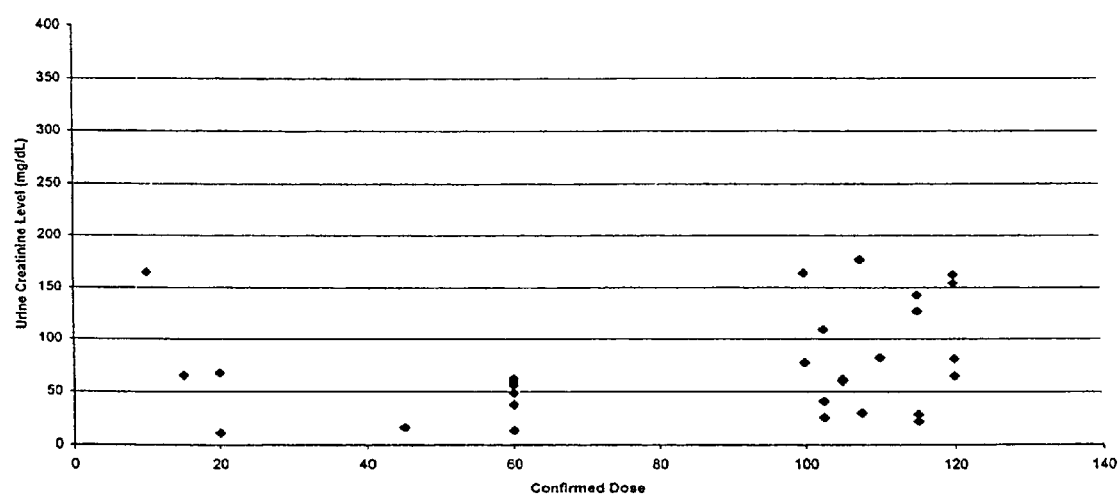
FIG. 2 is a graph showing uncorrected urine creatinine levels for confirmed daily methadone doses.

Uncorrected urinary EDDP metabolite and creatinine concentrations were quite variable and did not correlate well with known methadone doses as illustrated in FIGS. 1 and 2.

Figure 3:
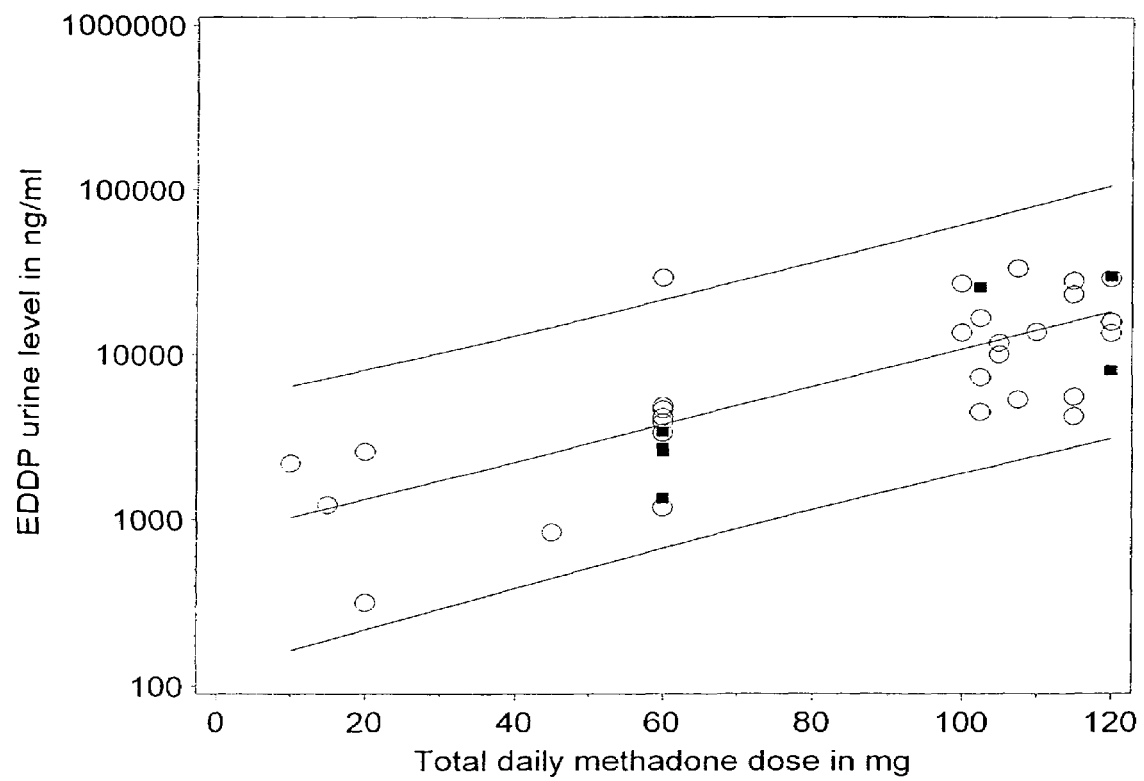
FIG. 3 is a graph plotting out the log of EDDP in urine sample versus confirmed total daily methadone dose with 95% prediction intervals.

For establishment of a regression model for the prediction of methadone intake from selected clinical parameters, the five urine screens assumed to be aberrant were excluded from the initial analysis leaving 30 (81%) available for modeling (two observations when patient was miscarrying were excluded from all analyses). Uncorrected urinary EDDP metabolite and creatinine concentrations were quite variable and did not correlate well with known methadone doses (FIGS. 1 and 2). When a regression model was formed with the log of EDDP, there was a significant relationship ($p<0.001$) as shown in FIG. 3.

Although the relationship was significant, the regression line explained less than 60% of the variability ($R^2=0.58$), and the log analysis did not differentiate compliant individuals who had been taking the medication on the day previous to testing from those who either did not take the medication the day previous to testing or those who had some problem with metabolism at the time of testing.

Figure 4:
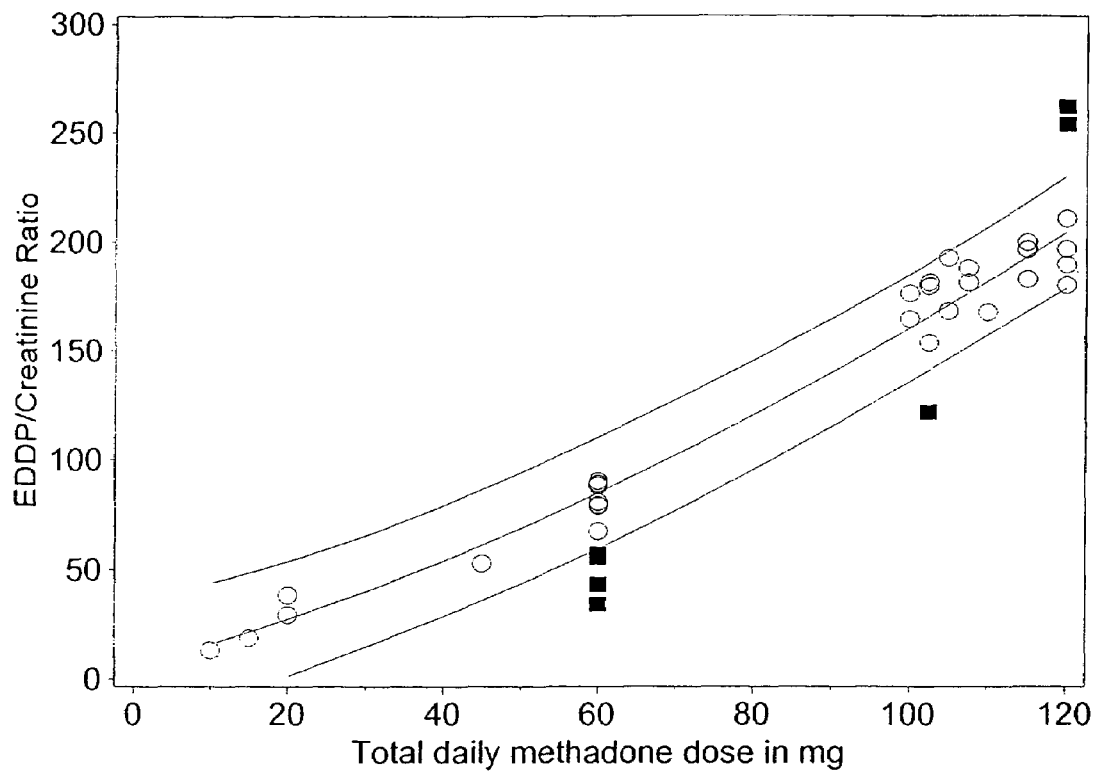
FIG. 4 is a graph showing a plot of laboratory EDDP/creatinine ratios versus prescribed total daily methadone doses revealing that known instances of nonadherance or unusual physiological factors affecting methadone metabolism fell outside of the 95% prediction intervals for the model and which were readily detected.

A substantially better predictive model was obtained for the EDDP/creatinine ratio. A quadratic model (EDDP/Creatinine=$5.48+0.98*Dose+0.0056*Dose^2$) fit the observed data significantly better than a linear model and provided an $R^2=0.97$ (FIG. 4). This means that 97% of the original variability was explained by the model, which was highly statistically significant ($p<0.001$).

Sensitivity to Known Outliers

The goal of the model was to be able to predict whether a patient had adhered to a prescribed dosage regimen. Plotting the laboratory determined EDDP/creatinine ratios from the known aberrant data against the prescribed (expected) methadone dose showed that these data fell outside of the 95% prediction limits for the quadratic model (FIG. 4). While the regression equation above produced excellent results, we sought to determine whether the predictive value of the model could be improved by considering patient characteristics that might affect the ratio. In that creatinine formation is directly proportional to total muscle mass, we considered age, body size (height, weight, BSA, BMI, and LBW), and gender, all of which factor into a person's muscle mass. None of these factors significantly improved the fitted model; although, with only seven patients in the analysis, our ability to assess any independent contribution of these factors was limited.

The results set forth above, clearly demonstrate that the use of a urine creatinine ratio when analyzing methadone metabolites in urine, substantially reduced the variability associated with the urine testing. Multivariate analysis revealed that any interindividual variations in muscle mass due to age, gender, height and weight, BMI or LBW are adequately represented by the urine creatinine levels only. No further correction for these factors was found to be of any benefit. The use of a urine creatinine ratio when analyzing methadone metabolites in urine explained a statistically significant and substantial proportion of the variability associated with the urine testing results. Aberrant methadone use or metabolism in the methadone maintenance patients was readily apparent. If this model is further validated, it could substantially benefit methadone maintenance programs by reducing the need for observer confirmation of doses and improving reliability in monitoring. A higher level of verifiable control may thereby be achieved. This model could substantially benefit methadone maintenance programs by reducing the need for observer confirmation of doses and improving monitoring reliability.

The results of the methadone study further verify previous literature reports that expressing urinary drug metabolite concentration as a ratio to the amount of creatinine can adequately control for urine volume fluctuations. The American Conference of Governmental Industrial Hygienists recommend that urine creatinine ranging between 20 and 350 mg/dL are valid (25). Normalizing urine drug concentrations to urine creatinine values has been attempted for drugs such as marijuana (26-29), amphetamine (30), cocaine (31), nicotine (32) and buprenorphine (33). Most of these applications, however, have been designed with the specific aim of avoiding false negative results in drug screening programs due to very dilute urine specimens (28, 34, 35).

The data used in this study was sufficient to yield a highly significant regression that allowed the demonstration of known outliers. Intra-individual variability in renal excretion of creatinine can be temporarily increased by meat consumption (14, 15, 39). This variability may account for 10%-29% between-day variation in calculated creatinine clearance for a given individual (16). These parameters were not considered in this study, but are expected to be considered in future studies.

Conclusions

Accordingly, it is envisioned that the methadone screening protocol of the present invention has the potential to enable providers to identify aberrant use patterns in patients (e.g., over or under using the medication). Additionally, urine metabolite/urine creatinine ratio could be applied to any drug that can be tested through urine, including opioids to provide for enhanced understanding of how a patient is taking that drug. This would be especially advantageous for medications that are taken on a timed basis (i.e., OxyContin®) and other drugs that have a high potential for misuse, abuse, or diversion due to high street value. Thus, by correcting fluctuations in urine dilution through metabolite/creatinine ratio determinations, the potential exists for the ability to test and monitor for patient methadone adherence across a range of clinically relevant dosages. It is expected that a similar approach may prove useful for other drug treatments as well.

To provide a fuller understanding of the scope of the present invention, the following prophetic examples are provided.

Example 2

Overuse of Opioid Medication

In this example, a patient in a methadone maintenance program was directed by the clinician to take 100 mg per day of methadone and was taking an observed daily dose of that amount. On Tuesday he arrived for his daily observed medicine and a urine screen was performed. The EDDP (methadone metabolite) was present in his urine at an extremely high level (e.g., 35000 ng/ml), which may or may not be consistent with his prescribed dose because hydration affects the amount of the metabolite found per ng/ml. The EDDP level in urine is highly variable and is not specifically correlated to dose of drug. His creatinine level (e.g., 20 mg/dL) indicated that he was quite well-hydrated. The drug metabolite was divided by creatinine level to produce the metabolite/creatinine ratio (e.g., 1750). This drug metabolite/creatinine ratio was found to correlate well with a drug-dose and a confidence interval for creatinine that is approximate to the dose of drug that would be appropriate for that ratio. This information was compared to normative tables and this amount was consistent with a daily methadone dose of 500 mg, an indication that this patient was gaining methadone from another source and using substantially larger amounts of methadone than has been prescribed at the methadone clinic. The drug metabolite/creatinine ratio has been helpful in identifying an aberrant use pattern for the above opioid addict. Under previous testing conditions, this patient would have been continued on that medication because he passed the positive-negative urine test. However, by using urine metabolite/urine creatinine ratio coupled with appropriate normative data, an approximate dose range based on the urine test was developed, which allowed the clinician to easily identify the aberrant use patterns. Accordingly, this novel analytical method enables the clinician to make a more accurate assessment of the situation before discontinuing the prescription.

Example 3

Underuse of Opioid Medication

In this example, a patient in a chronic pain program has been prescribed OxyContin® 60 mg every 12 hours, for a total daily dose of 120 mg. The patient arrives at the pain clinic for his regularly scheduled follow-up visit and a random urine screen is performed. The patient's urine screen reveals the drug metabolite oxycodone at a level of 1000 ng/ml and a creatinine level of 80 mg/dL. Generally because the OxyContin® metabolite was present in the urine during the urine screen the patient's medication would have been refilled and continued because the presence of the drug metabolite by itself has been shown to not be correlated to drug dose. The presence of the metabolite in the urine has simply been correlated with the fact that the patient has been taking the drug. However, by using the drug metabolite/creatinine ratio equal to 12.5, which is far too low for the drug dose in question. A review of normative data with this ratio suggests that the patient would have to be taking less than 10 mg of OxyContin® on a daily basis (or recently) to achieve that ratio level. This suggests that the patient has not been taking the medication in the way it has been prescribed and has either been 1) diverting the medication and had taken just a small dose of the medicine prior to the office visit to "pass" the positive/negative urine screen or 2) had been overtaking the medication (i.e., abusing the medicine) but had effectively run out of the medication and had saved 1 or 2 pills to take prior to the urine screen in order to "pass" the urine screen. Therefore, by using the method of the present invention, the patient's aberrant use pattern for OxyContin® was identified.

Example 4

Use of Multi-Level Urine Test Strips for Opioids

In this embodiment of the present invention, urine test strips may be used as an alternative to the standard GC-MS testing to detect and measure opioid levels in urine. It is envisioned that the urine strips would have detectable markings ranging from, for example, level 1 to level 10 for differentiating between multiple concentrations of prescribed drugs. It is expected that a one-sided multi-level urine strip, for example, depicted in FIG. 5, could be used where a patient has been prescribed 60 mg of OxyContin® to be taken every 12 hours, for a total daily dose of 120 mg. The patient which is in a chronic pain program then arrives at the pain clinic for a regularly scheduled follow-up visit at which a random urine screen is performed. The urine screen is carried out by submerging a one-sided flexible test strip in the patient's urine sample for a predetermined amount of time. The clinician may then visually observes the concentration of metabolite in a patient's system by reading the test strip.

In this case, the patient's urine screen reveals the drug metabolite oxycodone at a level greater than 1000 ng/ml but less than 1500 ng/ml (i.e., Level 3 on the oxycodone strip). When combined with a creatinine level via a creatinine test strip, which verifies a creatinine level greater than 70 mg/dL and less than 90 mg/dL (i.e., Level 6 on the creatinine strip). The clinician then is able to calculate a metabolite (level 3)/creatinine (level 6) ratio and with the aid of normative tables, quickly is able to identify that the patient's urine quantification does not match the prescribed drug dose, indicating aberrant use. These multi-level urine test strips are advantageous over the current "one threshold" model strips currently on the market that are used for general positive/negative drug testing, which simply detects the presence or absence of a drug at the predetermined threshold level. Thus, if a clinician were to use the current "one threshold" strips in this case, the patient's medication would be incorrectly refilled and continued.

Figure 6:
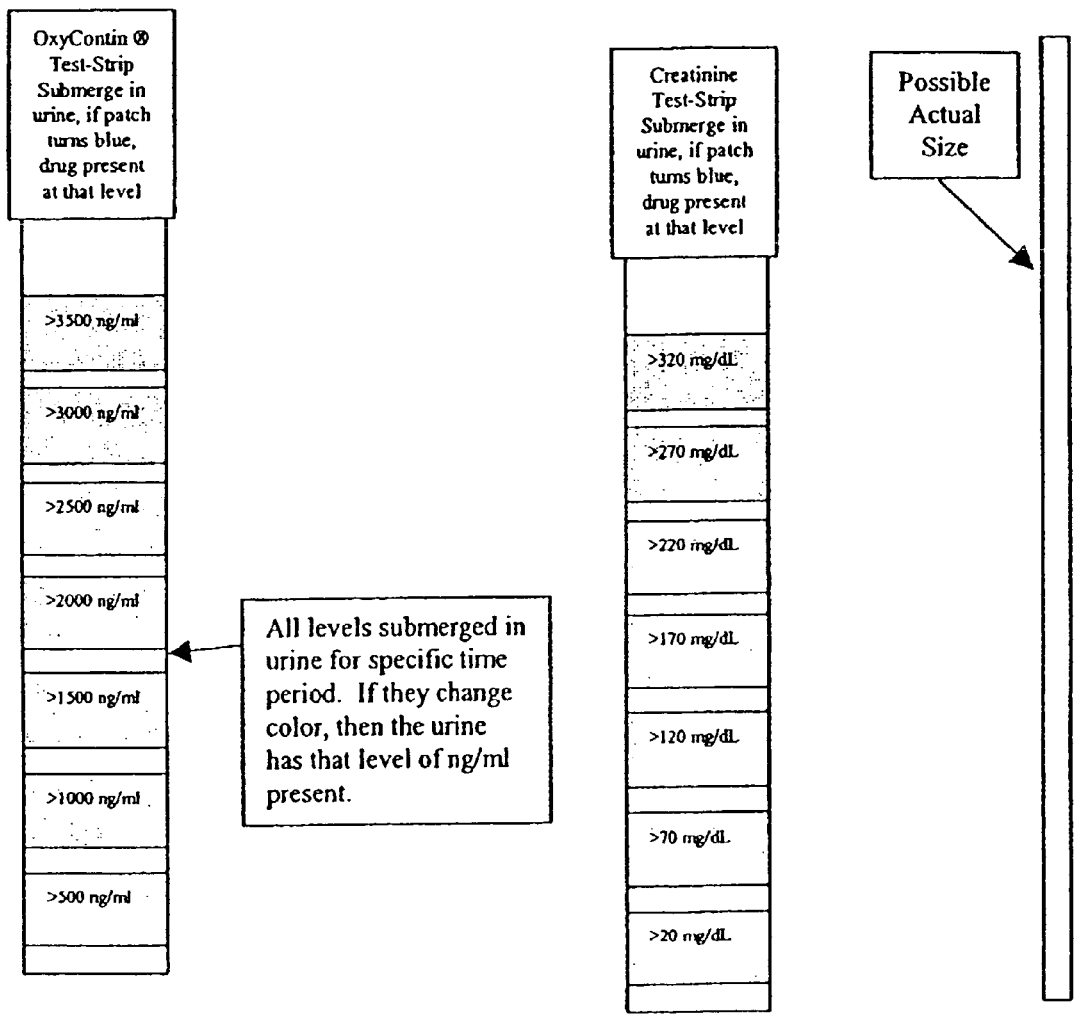
FIG. 6 depicts a flexible multi-level, vertical, two-sided test strip for determining metabolite concentration in urine.
Figure 7:
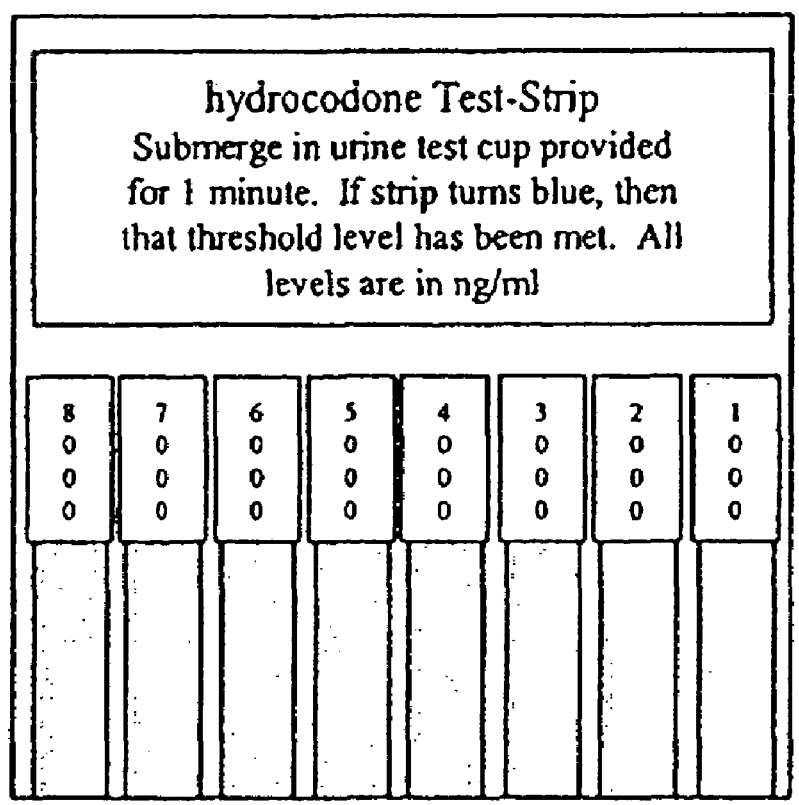
FIG. 7 depicts a flexible multi-level (horizontal) test strip for determining metabolite concentration in urine.

In another embodiment of the invention, depicted in FIG. 6, it is expected that a two-sided multi-level urine strip, would be suitable in a situation, where a clinician would like to test for more than one drug metabolites simultaneously using the same strip. In this scenario, the clinician would submerge the two sided flexible test strip in a biological sample (e.g., a urine sample, for a predetermined amount of time. The clinician may then visually observe the concentration of metabolite in a patient's system by reading the test strip. Applicants also envision that a multi-sided, multi-level urine test device (i.e., three-sided or more) may be useful in a situation where the clinician is interested in testing for aberrant use of a series of drugs.

Furthermore, it is envisioned that with the normative data developed for a number of different drugs, several multi-level urine test strips may be used simultaneously, in combination with each other to achieve maximum dose accuracy, to identify inappropriate drug use. Specifically, by using normative data a Level 3 oxycodone strip combined with a Level 6 creatinine strip would be most consistent with aberrant use of the prescribed medication. Presumably, the aberrant use would be the result of either 1) diverting the medication and taking just a small dose of the medicine prior to the office visit to "pass" the positive/negative urine screen; a result of 2) overtaking the prescribed medication (i.e., abusing the medicine) or a situation where the patient had effectively run out of the medication but had saved 1 or 2 pills to take in order to "pass" the urine screen. Thus, using the multi-level urine strips, the patient's aberrant use pattern would be readily identified by the clinician.

Example 5

Overuse of Benzodiazepines

In yet another example of the present invention, it is encompassed that a psychiatrist could prescribed Xanax® 1 mg prn up to tid for a patient to manage her chronic anxiety. The patient arrives at her normally scheduled follow-up visit and reports that she has been taking her medicine exactly as prescribed. She indicates that she has taken 1 mg tid for each of the last 3 days due to her intense anxiety. She denies ever taking more than three pills per day. She would like an increase in her dosage to help her with her intense anxiety. She is sent for a random urine screen and it reveals that her level of benzodiazepine metabolite for alprazolam is 5000 ng/ml. This would normally be considered appropriate and her prescription would be refilled. However, when creatinine is used to correct for hydration (i.e., 50 mg/dL), it is observed that the ratio from normative information is indicative of a person who is taking a dose between 2 mg tid and 2.5 mg tid. The psychiatrist discusses this with the patient and she admits that she has been getting Xanax® from multiple sources and feels that she is "addicted" to the medication. She is referred for inpatient drug treatment. Accordingly, under current testing conditions, because the patient passed the positive-negative urine test, the psychiatrist would have continued prescribing the same dosage or an increased dosage of the medication. However, by using urine metabolite/urine creatinine ratio with appropriate normative data, an approximate dose range based on the urine test was developed and was capable of easily identifying the aberrant use patterns of the patient.

Example 6

Overuse of Stimulants Identified by Multi-Level Urine Test Strips

In still another example of the present invention, it is encompassed that an adult male could be prescribed Ritalin® 10 mg tid (30 mg total daily) for management of Adult ADHD. A regularly scheduled urine testing is performed using multi-level urine test strips. The commonly observed Ritalin urinary metabolite is shown to be present in his system at a Level 6 (between a range of 3000 ng/ml and 3500 ng/ml), and creatinine is found to be present at Level 2 (between range of 20 ng/ml and 30 ng/ml). The normative values associated with this combination of test-strips is indicative of Ritalin® usage of between 60 mg total per day to 80 mg total per day, suggesting the patient is substantially overusing the medication. A pharmacy check is performed and reveals that this patient has been receiving Ritalin® from 3 different providers for several months. The patient is confronted with this information and appropriate treatment is started. Under current drug testing conditions, because this patient would have passed the positive-negative urine test, and would have continued to receive prescriptions for Ritalin®. Thus, by using drug metabolite/urine creatinine ratio with appropriate normative data, an approximate dose range based on the urine test was developed and easily identified the aberrant use patterns.

Example 7

Computer-Assisted Products Using Normative Data

In another embodiment of the present invention, it is envisioned that one skilled in the art would be able to enter patient-specific data (e.g., height, weight, age, sex, medication type, reported doses, GC-MS derived urine creatinine level, and drug metabolite urine level) into a computer-assisted product, such as a software program or a related data base; where the data would be compared to normative data for purposes of identifying aberrant drug use patterns in patients.

In one scenario, it could be expected that a patient, who is on long-term opioid medication for chronic low back pain attends a regular follow-up visit with her clinician and indicates that her medication (Kadian® 100 mg per 12 hrs) is not working well and she would like an increased dosage. She is 5'2" tall and weighs 140 pounds. A urine screen is performed utilizing GC-MS evaluation. The metabolite of Kadian® (i.e., morphine) is present in her system, suggesting the patient has been taking at least some of the medication. Creatinine is also measured as part of the urine screen. All of her relevant patient information (i.e., age, sex, height, weight, urine morphine level, urine creatinine level, and number of reported Kadian® doses taken over the past two days—4 doses at 100 mg) are input into the computer program or related database. The patient information is then analyzed and compared against a metabolite specific normative database that graphically plots a patient's actual data versus the normative data with confidence intervals via regression statistical analysis. From this graph it can be observed that the patient's level is inconsistent with her report of 4 doses over the past 48 hours. Her dose is suggestive of substantially more medication taken over the time period. Although, her pills were counted and were consistent with her prescriptions within the pain clinic, a pharmacy check identified that the patient has been receiving MS Contin® 75 mg per every 8 hours from another source and had likely been taking it in combination with the Kadian® 100 mg every 12 hours. Despite GC-MS testing capabilities that allow metabolite concentration measurements in the nanogram per milliliter levels, current urine testing methods still are unable to identify various concentrations of metabolites to determine aberrant drug usage patterns in patients.

Example 8

Other Computer-Assisted Products

In yet another embodiment of the present invention, a scenario is envisioned where one skilled in the art would be able to determine with accuracy the level of aberrant drug usage patterns in a patient who has been on long-term transdermal opioid medication (Duragesic Patch 200 mcg per 3 days). The patient has had previous clean urine screens but he appears to be slightly early for his regular refill. A urine screen is performed, with the addition of a kidney function test, as well as a skin permeability analysis. All of the data (e.g., age, sex, weight, height, overall muscle mass, estimate of proportion of carbohydrates to proteins consumed during prior 48 hours, which may affect creatinine level, dose of drug prior 2 days, last patch change, kidney function test, skin permeability analysis, urine creatinine level, and drug metabolite level are input in the computer program. The program then utilizes normative data and regression statistical methods to approximate drug dosage used in the recent past. It was determined that this patient had not been taking his medication as prescribed. Rather, the computer-generated analysis results for this patient reveal that in the past 48-hours a sudden large dose of the medication had been taken that is inconsistent with the transdermal route of administration admitted to by the patient. The patient had likely in the previous 48-hour period tampered with the patch delivery system and taken the medication through the oral route, generally referred to as, "sucking the ooze", which is known to lead to a substantial "high" on the street. Accordingly, this type of drug misuse would not have been identified with the current analytical tests on the market today. However, in accordance with the present invention the use of urine creatinine to correct for hydration, coupled with additional patient characteristics which allow for the variability in the regression analysis to be reduced, enables the identification of aberrant drug use through computer-assisted products with statistical analysis capabilities connected to a normative data base.

Example 9

Use of Slide-Rule or Dial Methods to Produce Confidence Intervals for Opioid Monitoring and/or other Drug Monitoring In another embodiment of the present invention, a scenario is envisioned where one skilled in the art would be able to determine with accuracy the level of aberrant drug usage patterns in a patient who is being medicated for a combination of chronic pain and adult ADHD by a rural physician. Given that the physician does not have the access to a drug screening laboratory, he utilizes multi-level urine test strips for testing of various medications. He has all his patients go through a standard protocol that first identifies a positive analysis of the medications and street drugs they have in their system. The above patient is positive for morphine and amphetamines, which is consistent with his prescriptions. The next set of test strips identifies that he is at a level 7 for morphine; level 10 for amphetamines; and level 4 for creatinine. Using a slide-rule developed from normative data for the type of morphine this patient is on (i.e., MS Contin®), the patient's level is consistent with his prescribed dosage. Using a slide-rule developed from normative data for the type of amphetamine this patient is on (i.e., Adderall XR®) the patient's level is suggestive of usage slightly higher than the prescribed amount. This is reviewed with the patient who admits that he had been feeling "drowsy" from the MS Contin® and had been taking a few extra doses of Adderall XR® to get through work. Discussion ensues and a decision is made to transition the patient into a different opioid that, hopefully, would not lead to the same amount of drowsiness as the MS Contin®. Patient is happy with the result. Again, the above scenario would not be possible with current urine testing protocols but with appropriate adjustment for hydration and normative data, the multi-level testing strips for the drug metabolite(s) and urine creatinine, combined with the slide rule to assess normative data enables quick, inexpensive and informed medical determination for a physician in a rural setting that does not have access to a fully functioning urine testing facility.

Example 10

Use of Monitoring Methods in Methadone Maintenance Programs

Currently, individuals with severe opioid addiction are often placed on a methadone program maintenance for anywhere between 4 months post-detoxification to the rest of their lifetime, to assist them in avoiding a relapse to their drug use habits. All methadone maintenance programs require daily observed doses, with occasional take-home doses for one weekend day or on holidays. Accordingly, the foregoing example describes the benefits of this novel testing methodology to reduce the need for daily observed doses.

In one scenario, a female patient on 100 mg of methadone per day for a methadone maintenance program was provided with a one-week supply of medicine. She would be called to submit a random urine screen. A requirement for continuing in the methadone maintenance program, on weekly take-home dosing, was that she would submit a urine sample within 12 hours of the phone call requesting that sample. She submits her sample as requested and her urine level for EDDP and creatinine are analyzed. The data obtained from the urine screen was compared to normative metabolite data for methadone wherein the patient was on a once daily dosing schedule. It is determined that the patient's drug metabolite/urine creatinine ratio is consistent with a dose between 30-50 mg of once daily dosing, indicating that this patient has been underusing her methadone on a daily basis. The comparative results obtained from the normative metabolite data allow the clinician to accurately identify dose dependent levels of patient drug use that current testing methods are incapable of determining. Applicants believe that the use of this new methodology may substantially change the landscape of methadone maintenance and allow for substantially reduced health care cost associated with daily observed dosing. Thus, under current methodology, the patient who tests positive for the presence of the urinary metabolite would have continued receiving daily-observed doses of methadone, despite her aberrant use patterns (i.e. "hoarding" medicine to use in large quantities or diverting it, as described hereinabove).

Example 11

Use of Computer Program, Internet Web-Based Calculator, or Intranet Calculator

In another embodiment, the invention provides a computer program, internet web-based calculator or an intranet calculator that would allow a medical provider, without direct access to computer software, to utilize the normative database, confidence intervals, and/or regression equations to improve accuracy in assessing results of a specific urine analysis. In this scenario, a medical provider would access a web-site or an intranet of a sponsoring clinic that would allow entry of meaningful data (e.g., metabolite levels, age, weight, creatinine level, etc.) and would provide confidence interval or regression equation outcome. It is encompassed within the scope of this invention that one skilled in the area could further develop a computer program or conversion algorithm that would allow for conversion of one type of urine testing protocol or analysis to another type within an organization (e.g., clinic) or between multiple organizations (e.g., several clinics).

Example 12

Use of Computer Program, Internet Web-Based Calculator, or Intranet Calculator with Self-Correction In another embodiment, the invention provides a computer program, internet web-based calculator or an intranet calculator that would allow for data to be added into a normative database to improve the accuracy of the database and subsequent confidence intervals and/or regression equations. Currently, normative databases are developed from specific research projects that are limited to a specific number of observations, with appropriate controls placed on each observation. These controls are placed to ensure that the observations are consistent with the overall population they are meant to represent. With the development of appropriate technology and the participation of a large group of medical providers, the need for those controls would diminish because the study population would actually be the same as the actual population. This would thereby provide a true normative dataset that would enhance our confidence intervals and regression equations. With the addition of a "self-correcting" component in the database, meaning each new observation added would become part of the database and further adjust the database elements (e.g., regression equation, confidence intervals, means, standard deviations, error, etc.), the database would become a self-adjusting database. This allows the database to become more representative of the actual population as time progresses. This would lead to improved accuracy in the predictions, confidence intervals, and regression equations that come from that dataset.

Example 13

Use of Covariates to Develop a Regression Model with OxyContin® and Oxycodone that can Later be Used for Prediction of Dose Confidence Interval This embodiment of the invention provides for a retrospective study performed as described in Example 1 above, without the observed doses. It is noted that this study utilized retrospective data following the same appropriate research analyses found in Example 1 with IRB approval. In this example, there were 27 valid observations for modeling. Thirteen observations are dropped due to one or more of the following reasons: 1) metabolite result outside the limits; 2) non-compliance; and/or 3) one of the conditions hepatitis, impaired kidney function, or amputee. In addition, two patients (IDs 231 and 235) with four observations were excluded from modeling due to documented non-compliance.

Figure 9:
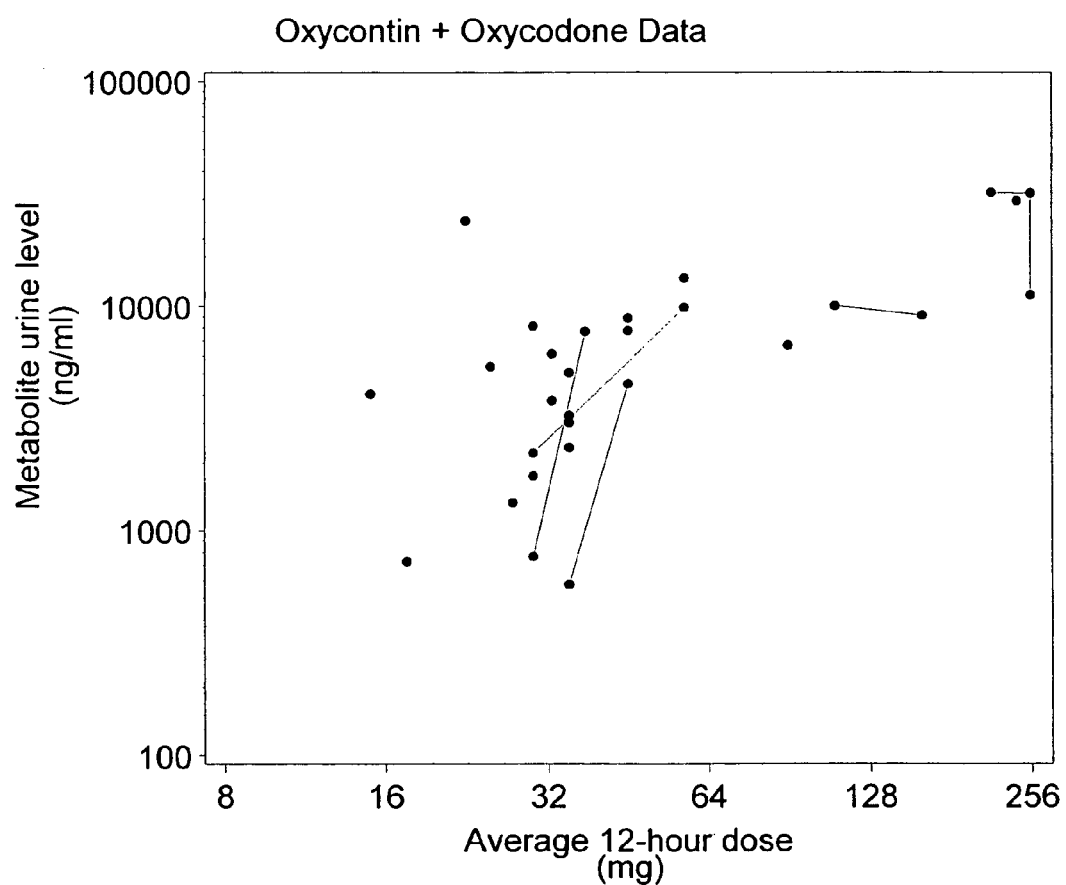
FIG. 9 is a graph showing uncorrected urine oxycodone (from OxyContin® and/or oxycodone) for confirmed OxyContin® and/or oxycodone medication combinations.
Figure 10:
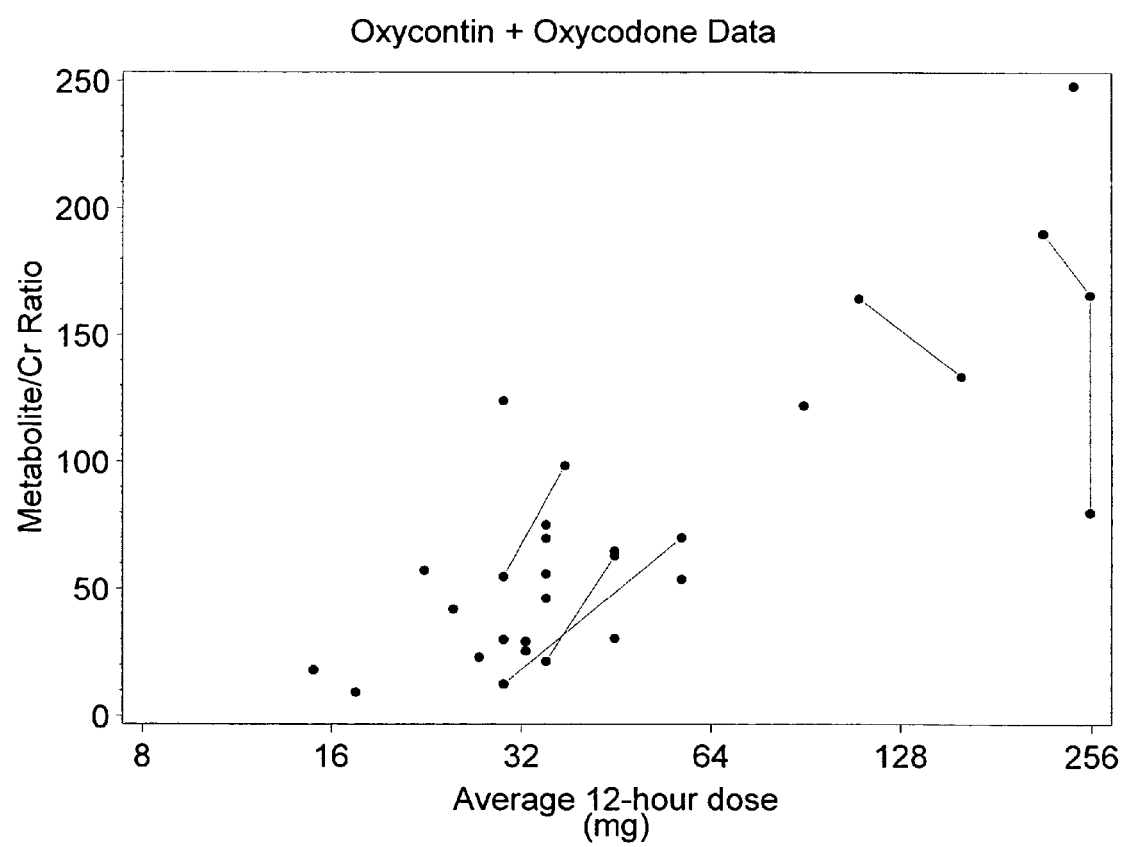
FIG. 10 is a graph showing creatinine corrected urine oxycodone for confirmed OxyContin® and/or oxycodone medication combinations.

FIG. 9 and FIG. 10 show the raw data for the metabolite vs. dose and the metabolite/creatinine ratio vs. dose, respectively. A model for metabolite vs. the dose (both on log scales) with the urine creatinine as a covariate is substantially better than a model using the metabolite/creatinine ratio as the response ($R^2$=0.78 vs. about 0.64, respectively). Both dose and creatinine are highly significant in the metabolite model ($p<0.001$).

Figure 11:
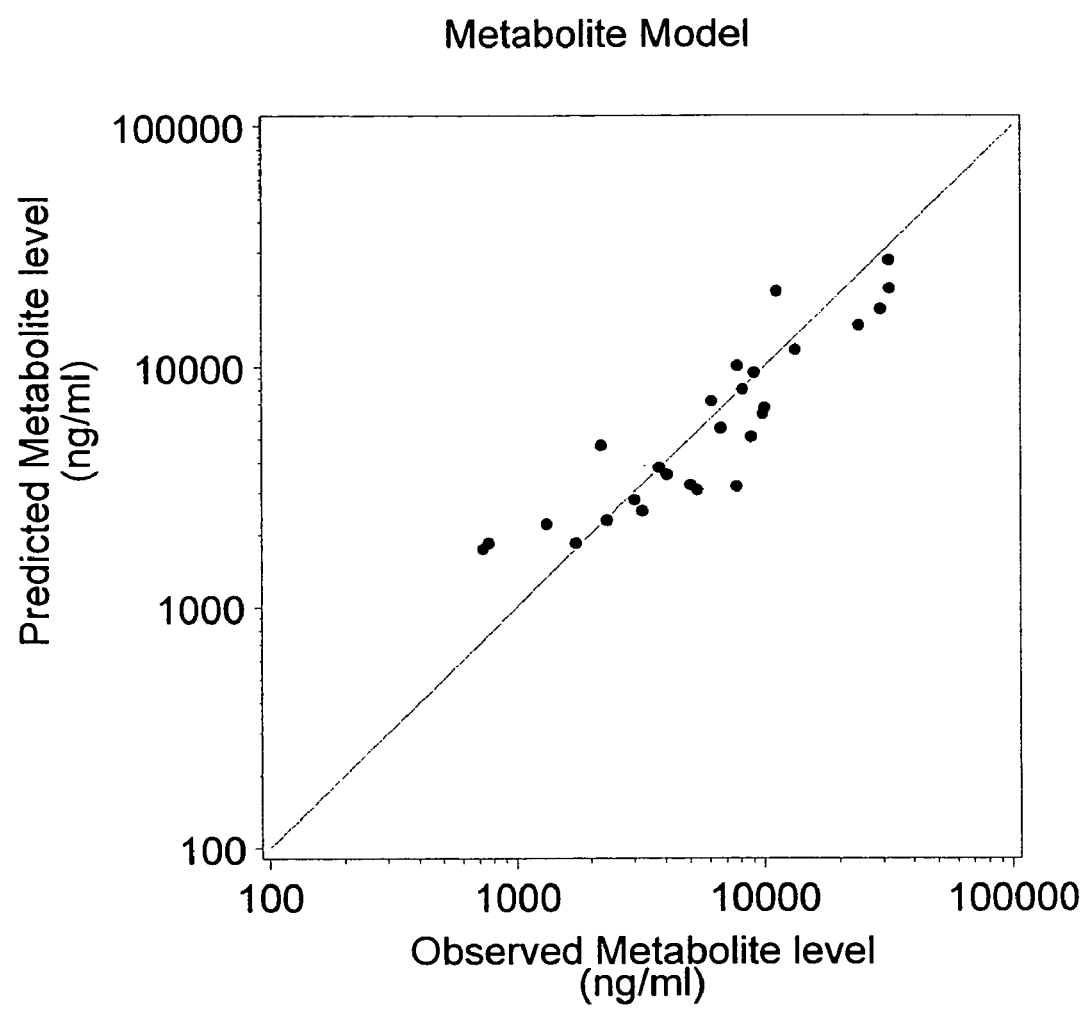
FIG. 11 is a regression equation with predicted versus observed metabolit concentration for the model for the metabolite (oxycodone from either OxyContin®, oxycodone, or both combined) as a function of dose and creatinine.

Furthermore, FIG. 11 shows a plot of predicted vs. observed for the model for the metabolite as a function of dose and creatinine. With regard to covariates in the OxyContin® and Oxycodone model, gender and weight provide no real contribution to the model for the metabolite as a function of dose and creatinine. Age shows some marginal association ($p=0.062$), but the adjusted $R^2$ decreases from 0.78 to 0.76.

Applicants note that this example displays the potential benefit of this model even when creatinine is a co-variant and not a primary element in the regression model. In this model, similar to Example 1, it is envisioned that with sufficient numbers of observations it will be possible to properly assess via statistical analysis whether any one observation is within the appropriate confidence intervals as noted by the regression model and use of identified co-variants.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

REFERENCES

1. Barbanel C S, Winkelman J W, Fischer G A, King A J; Confirmation of the Department of Transportation Criteria for a substituted urine specimen. J Occup Environ Med (2002) 44:407-416.
2. Kapur B, Hershkop S, Koren G, Gaughan V; Urine fingerprinting: detection of sample tampering in an opiate dependency program. Ther Drug Monit (1999) 21:243-250.
3. Kintz P, Tracqui A, Mangin P, Edel Y; Sweat testing in opioid users with a sweat patch. J Anal Toxicol (1996) 20:393-397.
4. Preston K L, Huestis Mass., Wong C J, Umbricht A, Goldberger B A, Cone E J; Monitoring cocaine use in substance-abuse-treatment patients by sweat and urine testing. J Anal Toxicol (1999) 23:313-322.
5. Ready L B, Sarkis E, Turner J A; Self-reported vs. actual use of medication in chronic pain patients. Pain (1982) 12: 285-294.
6. Berndt S, Maier C, Schutz H W; Polymedication and medication compliance in patients with chronic non-malignant pain. Pain (1993) 52: 1-9.
7. Sees K L and Clark H W Jr.; Opioid use in the treatment of chronic pain: assessment of addiction. Journal of Pain and Symptom Management (1993) 8(5): 257-264.

8. Chabal C, Erjavec M K, Jacobson L, et al.; Prescription opiate abuse in chronic pain patients: clinical criteria, incidence and predictors. The Clinical Journal of Pain (1997) 13: 150-155.
9. Fishman S M, Bandman T B, Edwards A, et al.; The Opioid contract in the management of chronic pain. Journal of Pain Symptom Management (1999) 18: 27-37.
10. Belgrade M; Urine toxicology testing in patients with chronic pain. Abstract present at the American Pain Society Annual Meeting, Phoenix, Ariz., (April, 2001).
11. Fanciullo D A, Katz N; The role of urine toxicology screening in patients on chronic Opioid therapy. Abstract presentat at the American Acaddemo fo Pain Meicaone, (February, 2001).
12. Katz N and Fanciullo G J; Role of urine toxicology testing in the management of chronic Opioid therapy. The Clinical Journal of Pain (2002) 18: S76-S82.
13. Hawks R L; Developments in cannabinoid analysese of body fluids: implications for forensic applications. In The Cannabinoids: Chemical, Pharmacologic and Therapeutic Aspects. S. Agurell, W. Dewey and R. Willette, eds. Academic Press, Rockville, Md., (1983) pp 1-12.
14. Bingham S A, Cummings J H; The use of creatinine output as a check on the completeness of 24-hour urine collections. Hum Nurt: Clin Nutr (1985) 39C: 343-355.
15. Alessio L, Berlin A Dell'Orto A, et al.; Reliability of urinary creatinine as a parameter used to adjust values of urinary biological indicators. Int Arch Occup Environ Health (1985) 55: 99-106.
16. Narayanan S, Appleton H D; Creatinine: a review. Clinical Chemistry (1980) 26:1119-1126.
17. Wilkins J N; Quantitative urine levels of cocaine and other substances of abuse. NIDA Res Monogr. (1997) 175:235-52.
18. Baugh L D, Liu R H, Walia A S; Simultaneous gas chromatography/mass spectrometry assay of methadone and 2-ethyl-1,5-dimethyl-3,3-diphenylpyrrolidine (EDDP) in urine. J Forensic Sci (1991) 36:548-555.
19. Galloway F R, Bellet N F; Methadone conversion to EDDP during GC-MS analysis of urine samples. J Anal Toxicol (1999) 23:619-619.
20. George S, Parmar, S, Meadway C, Braithwaite R A; Application and validation of a urinary methadone metabolite (EDDP) immunoassay to monitor methadone compliance. Ann Clin Biochem (2000) 37:350-354.
21. Sporkert F, Pragst F; Determination of methadone and its metabolites EDDP and EMDP in human hair by headspace solid-phase microexecution and gas chromatography-mass spectrometry. J Chromatogr Biomed Sci Appl (2000) 746: 255-264.?
22. Steppan D D, Werner J, Yeater R P; Essential Regression 97 software accompanying Essential Regression and Experimental Design for Chemists and Engineers. Available for download at http://www.geocities.com/SiliconValley/Network/1032/CGPage1.html. (accessed Jul. 31, 2003)
23. Mosteller R D; Simplified calculation of body surface area. N Engl J Med (1987) 317:1098.
24. Halls M D; Formulas for calculating body surface area (BSA). http://www.halls.md/body-surface-area/refs.htm. (accessed Jul. 31, 2003)
25. American Conference of Government Industrial Hygienists. TLVs and BEIs: Threshold limit values for chemical substances and physical agents and biological exposure indices. Cincinnati (OH): ACGIH; (2000).
26. Manno J, et al.; Urine excretion patterns of cannabinoids and the clinical application of the EMIT-dau cannabinoid urine assay for substance abuse treatment. In: Agurell S, Dewey W E, Willet R E (eds). The Cannabinoids: Chemical Pharmacologica and therapeutic aspects, Academic Press: New York. (1984) p 281.
27. Painter P C, Evans J H, Greenwood J D, Fain W W; Urine cannabinoids monitoring. Diag Clin Testing (1989) 27: 29-33.
28. Lafolie P, et al.; Importance of creatinine analyses of urine when screening for abused drugs. Clinical Chemistry (1991) 37: 1927-1931.
29. Bell R, Taylor E H, Ackerman B, Pappas A A; Interpretation of urine quantitative 11-nor-delta-9-tetrahyrdocannabinoid-9-carboxylic acid to determine abstinence form marijuana smoking. Clinical Toxicology (1989) 27: 109-115.
30. Haberny K A, Walsh S L, Ginn D H, et al.; Absence of cocaine interactions with the MAO-B inhibitor selegiline. J Drug Alcohol Depend (1995) 39: 55-62.
31. Weiss R D, Gawin F H; Protracted elimination of cocaine metabolites in long-term, high-dose cocaine users. American Journal of Medicine (1988) 85:879-880.
32. Thompson S G, Barlow R D, Wald N J et al.; How should urinary cotinine concentration be adjust for urinary creatinine concentration? Clinical Chemistry Acta (1993) 187: 289-296.
33. Watson I D; Analysis of commonly abused drugs in urine at selected threshold (cutoff) concentrations (letter). Clinical Chemistry (1992) 38:441.
34. Needleman S, et al.; Creatinine analyses in single collection urine specimens. Journal of Forensic Sciences (1992) 37:1125-1133.
35. Cone E. et al.; In vivo adulteration: Excess fluid ingestion causes false-negative marijuana and cocaine urine tests results. Journal of Analytical Toxicology (1998) 22: 460-473.
36. Huestis M, Cone E; Differentiating new marijuana use from residual drug excretion in occasional marijuana users. Journal of Analytical Toxicology (1998) 22: 445-454.
37. Fraser A D, Worth D; Urinary excretion profiles of 11-nor-9-carboxy-Delta9-tetrahydrocannabinol: a Delta9-THC—COOH to creatinine ratio study #2. Forensic Sci Int (2003) 133:26-31.
38. Cone E; Predicating the amount of illicit cocaine use from benzoylecgonine and creatinine concentrations in a single urine specimen. Journal of Analytical Toxicology (1997) 21:83.
39. Tietz N; Textbook of Clinical Chemistry, Philadelphia, WB Saunders Co, (1986) 1279-1290.
40. Miller R C et al.; Comparison of specific gravity and creatinine for normalizing urinary reproductive hormone concentrations. Clinical Chemistry (2004) 50:5, 924-932.
41. Haddow J E et al.; Replacing creatinine measurements with specific gravity values to adjust urine cotinine concentrations. Clinical Chemistry (1994) 40:4, 562-564.
42. Preston K L et al.; Methadone and metabolite urine concentrations in patients maintained on methadone. Journal of Analytical Toxicology; (September 2003) 7, 332-341.
43. Kim H et al.; Relationship between environmental tobacco smoke and urine cotinine levels in passive smoke at their residence. Journal of Exposure Analysis and Environmental Epidemiology; (2004) 14, S65-S70.
44. Fraser A. Zamecnik J; Impact of lowering the screening and confirmation cutoff values for urine drug testing based on dilution indicators. Therapeutic Drug Monitoring; (2003) 25:6, 723-727.

45. Greenberg G N Levine R J; Urinary creatinine excretion is not stable: A new method for assessing urinary toxic substance concentrations. Journal of Occupational Medicine; (1989) 31:10, 832-838.

46. Fraser A Zamecnik J; Substance abuse monitoring by the correctional service of Canada. Therapeutic Drug Monitoring, (2002) 24: 187-191.

We claim:

1. A method for quantifying at least one metabolite in a biological sample comprising the steps of:
   (a) providing one biological sample obtained from a patient on a prescribed medication regimen, wherein the sample comprises at least one test metabolite, wherein in the sample is urine;
   (b) providing one set of known normative data specific to a reference metabolite, wherein the set of data is collected from a population that is on a prescribed medication regimen;
   (c) contacting the biological sample with an analytical device;
   (d) detecting the presence of at least one test metabolite in the biological sample with the device, wherein the device is capable of measuring the concentration of the test metabolite in the sample;
   (e) normalizing the biological sample to adjust for changes in the patient's hydration status by determining the metabolite/creatinine ratio of the patient; and
   (f) quantifying the concentration of at least one test metabolite in the biological sample by comparing a ratio between the concentration of the test metabolite from the patient to the set of known normative data specific to the reference metabolite concentration.

2. The method of claim 1, wherein the test metabolite to be quantified is selected from the group consisting of oxycodone, morphine, codeine, 2-ethylidene-1,5-dimethyl-3,3-diphenylpyrrolidone (EDDP), fentanyl, propoxyphene, hydrocodone, amphetamine, diazepam/temazepam, alphahydroxyalprazolam, and lorazepam.

3. A method of monitoring nonadherence to a prescribed medication regimen comprising the steps of:
   (a) providing one biological sample obtained from a patient on a prescribed medication regimen, wherein the sample comprises at least one test metabolite, wherein in the sample is urine;
   (b) providing one set of known normative data specific to a reference metabolite, wherein the set of data is collected from a population that is on a prescribed medication regimen;
   (c) contacting the biological sample with an analytical device;
   (d) detecting the presence of at least one test metabolite in the biological sample with the device, wherein the device is capable of measuring the concentration of the test metabolite in the sample;
   (e) normalizing the biological sample to adjust for changes in the patient's hydration status by determining the metabolite/creatinine ratio of the patient; and
   (f) quantifying the concentration of at least one test metabolite in the biological sample by comparing a ratio between the concentration of the test metabolite from the patient to the set of known normative data specific to the reference metabolite concentration determining non-adherence to a prescribed medication regimen, wherein the ratio between the test metabolite concentration and the reference metabolite concentration is used to identify nonadherence to a prescribed medication regimen, and wherein non-adherence is defined as overuse or underuse of the prescribed medication.

4. A method for quantifying at least one metabolite in a biological sample comprising the steps of:
   (a) providing one biological sample obtained from a patient on a prescribed medication regimen, wherein the sample comprises at least one test metabolite, wherein in the sample is urine;
   (b) providing one set of known normative data specific to a reference metabolite, wherein the set of data is collected from a population that is on a prescribed medication regimen;
   (c) contacting the biological sample of step (a) with an analytical device;
   (d) detecting the presence of at least one test metabolite in the biological sample with the device, wherein the device is capable of measuring the concentration of the test metabolite in the sample;
   (e) normalizing the biological sample to adjust for changes in the patient's hydration status by determining the metabolite/creatinine ratio of the patient; and
   (f) quantifying the concentration of at least one test metabolite in the biological sample by comparing a ratio between the concentration of the test metabolite from the patient to the set of known normative data specific to the reference metabolite concentration, wherein the test metabolite to be quantified is selected from the group consisting of oxycodone, morphine, codeine, 2-ethylidene-1,5-dimethyl-3,3-diphenylpyrrolidone (EDDP), fentanyl, propoxyphene, hydrocodone, amphetamine, diazepam/temazepam, alphahydroxyalprazolam, and lorazepam.

\* \* \* \* \*

UNITED STATES PATENT AND TRADEMARK OFFICE
CERTIFICATE OF CORRECTION

PATENT NO.      : 7,585,680 B2                                           Page 1 of 1
APPLICATION NO. : 10/924105
DATED           : September 8, 2009
INVENTOR(S)     : Larson et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1109 days.

Signed and Sealed this

Fourteenth Day of September, 2010

David J. Kappos
*Director of the United States Patent and Trademark Office*

(12) EX PARTE REEXAMINATION CERTIFICATE (9737th)
United States Patent
Larson et al.

(10) Number: US 7,585,680 C1
(45) Certificate Issued: Jul. 2, 2013

(54) METHOD AND DEVICE FOR MONITORING MEDICATION USAGE

(75) Inventors: Michael E. M. Larson, Minocqua, WI (US); Thomas M. Richards, Minocqua, WI (US)

(73) Assignee: Marshfield Clinic, Marshfield, WI (US)

Reexamination Request:
 No. 90/012,247, Apr. 10, 2012

Reexamination Certificate for:
 Patent No.: 7,585,680
 Issued: Sep. 8, 2009
 Appl. No.: 10/924,105
 Filed: Aug. 23, 2004

Certificate of Correction issued Sep. 14, 2010

Related U.S. Application Data

(60) Provisional application No. 60/499,129, filed on Aug. 28, 2003.

(51) Int. Cl.
 *G01N 31/22* (2006.01)
 *G01N 33/94* (2006.01)
(52) U.S. Cl.
 CPC .............. *G01N 33/94* (2013.01); *Y10S 436/808* (2013.01); *Y10S 436/901* (2013.01)

USPC ........... 436/169; 436/111; 436/171; 436/808; 436/901

(58) Field of Classification Search
 None
 See application file for complete search history.

(56) References Cited

To view the complete listing of prior art documents cited during the proceeding for Reexamination Control Number 90/012,247, please refer to the USPTO's public Patent Application Information Retrieval (PAIR) system under the Display References tab.

*Primary Examiner* — Elizabeth McKane

(57) ABSTRACT

The present invention provides methods for detecting and quantifying metabolites in a biological sample by measuring the concentration of a test metabolite in the sample and comparing that concentration against the concentration of the reference metabolite; enabling accurate metabolite concentration measurements to determine aberrant drug usage patterns. Also disclosed is an analytical testing device and related computer-assisted products for detecting and quantifying metabolites in a biological sample efficiently and accurately.

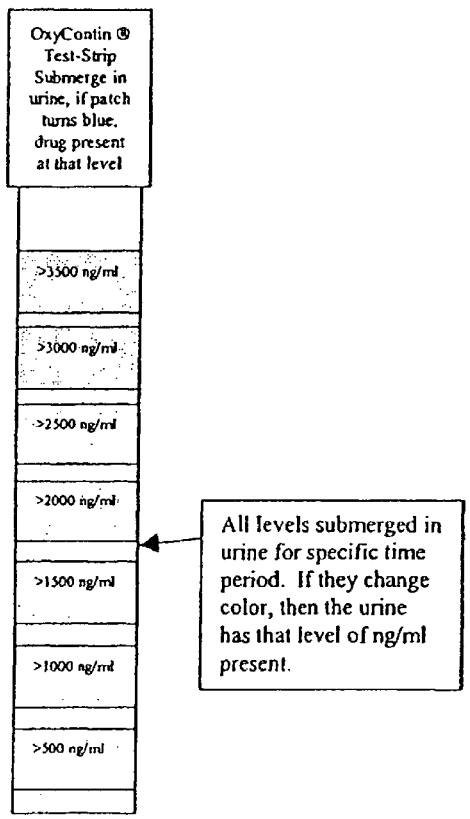

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1-4 is confirmed.

New claims 5-20 are added and determined to be patentable.

*5. The methods of claim 1, wherein the reference metabolite and the at least one test metabolite are oxycodone.*

*6. The methods of claim 1, wherein the reference metabolite and the at least one test metabolite are morphine.*

*7. The methods of claim 1, wherein the reference metabolite and the at least one test metabolite are hydrocodone.*

*8. The method of claim 1, further comprising the step of using the concentration of the at least one test metabolite quantified by comparing the ratio between the concentration of the at least one test metabolite from the patient to the set of known normative data specific to the reference metabolite to monitor possible non-adherence to a prescribed medication regimen.*

*9. The method of claim 1, wherein the set of known normative data is used to develop a regression model derived from two or more variables from the set of known normative data, wherein a first of the two or more variables is a ratio of urinary reference metabolite/creatinine concentration, wherein the regression model defines one or more variable-specific confidence intervals, and wherein step (f) is performed using the regression model.*

*10. The method of claim 1, wherein the test metabolite to be quantified is selected from the group consisting of oxycodone, morphine, codeine, fentanyl, propoxyphene, hydrocodone, amphetamine, diazepam/temazepam, alphahydroxyalprazolam, and lorazepam.*

*11. The methods of claim 3, wherein the reference metabolite and the at least one test metabolite are oxycodone.*

*12. The methods of claim 3, wherein the reference metabolite and the at least one test metabolite are morphine.*

*13. The methods of claim 3, wherein the reference metabolite and the at least one test metabolite are hydrocodone.*

*14. The method of claim 3, wherein the set of known normative data is used to develop a regression model using two or more variables from the set of known normative data, wherein a first of the two or more variables is a ratio of urinary reference metabolite/creatinine concentration, wherein the regression model defines one or more variable-specific confidence intervals, and wherein step (f) is performed using the regression model.*

*15. The method of claim 3, wherein the at least one test metabolite is selected from the group consisting of oxycodone, morphine, codeine, fentanyl, propoxyphene, hydrocodone, amphetamine, diazepam/temazepam, alphahydroxyalprazolam, and lorazepam.*

*16. The methods of claim 4, wherein the reference metabolite and the at least one test metabolite are oxycodone.*

*17. The methods of claim 4, wherein the reference metabolite and the at least one test metabolite are morphine.*

*18. The methods of claim 4, wherein the reference metabolite and the at least one test metabolite are hydrocodone.*

*19. The method of claim 4, further comprising the step of using the concentration of the at least one test metabolite quantified by comparing the ratio between the concentration of the test metabolite from the patient to the set of known normative data specific to the reference metabolite to monitor possible non-adherence to a prescribed medication regimen.*

*20. The method of claim 4, wherein the set of known normative data is used to develop a regression model using two or more variables from the set of known normative data, wherein a first of the two or more variables is a ratio of urinary reference metabolite/creatinine concentration, wherein the regression model defines one or more variable-specific confidence intervals, and wherein step (f) is performed using the regression model.*

\* \* \* \* \*

(12) EX PARTE REEXAMINATION CERTIFICATE (10226th)
United States Patent
Larson et al.

(10) Number: US 7,585,680 C2
(45) Certificate Issued: Jul. 21, 2014

(54) METHOD AND DEVICE FOR MONITORING MEDICATION USAGE

(75) Inventors: Michael E. M. Larson, Minocqua, WI (US); Thomas M. Richards, Minocqua, WI (US)

(73) Assignee: Marshfield Clinic, Marshfield, WI (US)

Reexamination Request:
No. 90/012,868, Jun. 11, 2013

Reexamination Certificate for:
Patent No.: 7,585,680
Issued: Sep. 8, 2009
Appl. No.: 10/924,105
Filed: Aug. 23, 2004

Reexamination Certificate C1 7,585,680 issued Jul. 2, 2013

Certificate of Correction issued Sep. 14, 2010

Related U.S. Application Data

(60) Provisional application No. 60/499,129, filed on Aug. 28, 2003.

(51) Int. Cl.
*G01N 31/22* (2006.01)
*G01N 33/94* (2006.01)

(52) U.S. Cl.
CPC ............. *G01N 33/94* (2013.01); *Y10S 436/808* (2013.01); *Y10S 436/901* (2013.01)
USPC ........... 436/169; 436/111; 436/171; 436/808; 436/901

(58) Field of Classification Search
None
See application file for complete search history.

(56) References Cited

To view the complete listing of prior art documents cited during the proceeding for Reexamination Control Number 90/012,868, please refer to the USPTO's public Patent Application Information Retrieval (PAIR) system under the Display References tab.

*Primary Examiner* — Elizabeth McKane

(57) ABSTRACT

The present invention provides methods for detecting and quantifying metabolites in a biological sample by measuring the concentration of a test metabolite in the sample and comparing that concentration against the concentration of the reference metabolite; enabling accurate metabolite concentration measurements to determine aberrant drug usage patterns. Also disclosed is an analytical testing device and related computer-assisted products for detecting and quantifying metabolites in a biological sample efficiently and accurately.

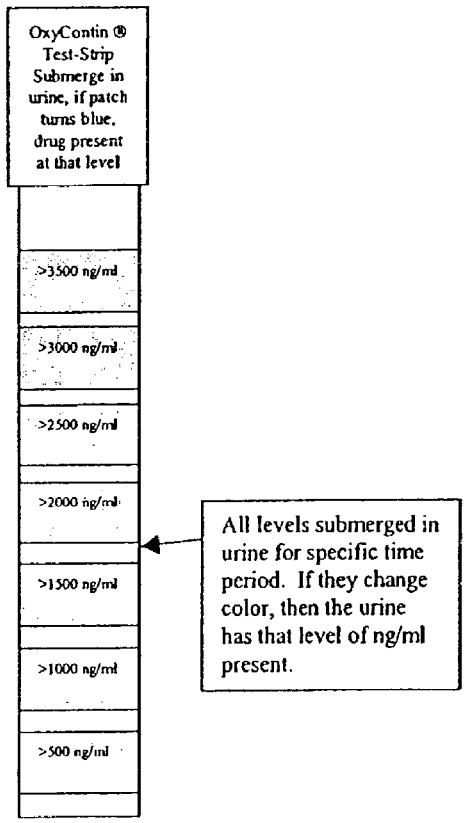

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-20 is confirmed.

\* \* \* \* \*